United States Patent [19]

Suzuki et al.

[11] 4,447,256

[45] May 8, 1984

[54] N-(UNSUBSTITUTED OR SUBSTITUTED PYRIDYL)AMINOMETHYLENE-DIPHOSPHONIC ACIDS, HERBICIDAL COMPOSITIONS CONTAINING SAME, THEIR USE FOR HERBICIDES, AND PROCESS FOR PREPARING SAME

[75] Inventors: Fumio Suzuki, Funabashi; Yoshihiro Fujikawa, Tokyo; Susumu Yamamoto, Narashino; Hidemi Mizutani, Funabashi; Tunehiko Ohya, Ageo; Takashi Ikai, Tokyo; Toshihiko Oguchi, Urawa, all of Japan

[73] Assignee: Nissan Chemical Industries, Ltd., Tokyo, Japan

[21] Appl. No.: 173,357

[22] Filed: Jul. 29, 1980

Related U.S. Application Data

[63] Continuation-in-part of Ser. No. 926,387, Jul. 20, 1978, abandoned.

[30] Foreign Application Priority Data

Jul. 20, 1977 [JP] Japan .................. 52-86098
Jul. 27, 1977 [JP] Japan .................. 52-89910

[51] Int. Cl.³ .................... A01N 57/16; C07D 213/72
[52] U.S. Cl. ............................ 71/86; 546/290; 546/292; 546/296; 546/297; 546/307; 546/308; 546/309; 546/310; 546/312
[58] Field of Search .................. 71/86; 546/290, 292, 546/304, 312

[56] References Cited

U.S. PATENT DOCUMENTS 3,658,506  4/1972  Kleiman et al. .................. 71/86 X
4,029,696  6/1977  Sommer et al. .................. 260/502.5
4,101,654  7/1978  Redmore ........................... 71/94 X
4,124,371  11/1978 Dixon ............................... 71/86 X

FOREIGN PATENT DOCUMENTS 1508772  4/1978  United Kingdom .

OTHER PUBLICATIONS

Plöger et al., Z. Anorg. Allg. Chem., vol. 389, (1972), pp. 119–128.

Primary Examiner—Catherine L. Mills
Attorney, Agent, or Firm—Parkhurst & Oliff

[57] ABSTRACT

N-(Unsubstituted or substituted pyridyl)aminomethylene-diphosphonic acids represented by the formula:

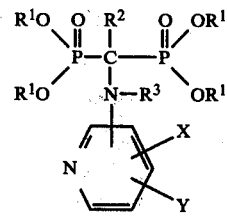

wherein each of $R^1$, $R^2$ and $R^3$ is independently hydrogen or lower alkyl, and each of X and Y is independently hydrogen, halogen, nitro, acetamino, carboxyl, lower alkyl, methoxycarbonyl, hydroxyl or methoxy, and salts thereof, have effective herbicidal effects on postemergence of plants and selective inactivity against cotton plants.

15 Claims, No Drawings

N-(UNSUBSTITUTED OR SUBSTITUTED PYRIDYL)AMINOMETHYLENE-DIPHOSPHONIC ACIDS, HERBICIDAL COMPOSITIONS CONTAINING SAME, THEIR USE FOR HERBICIDES, AND PROCESS FOR PREPARING SAME

This is a continuation-in-part application of U.S. patent application Ser. No. 926,387 filed July 20, 1978, now abandoned entitled: "N-Pyridylaminomethylene-diphosphonic acid compounds, herbicides containing them and process of producing these compounds".

The present invention relates to N-(unsubstituted or substituted pyridyl)aminomethylene-diphosphonic acid compounds, herbicidal compositions containing the same as an active ingredient, a method of use of the same as a herbicide, and a process for producing the same.

One aspect of the present invention provides compounds of the formula:

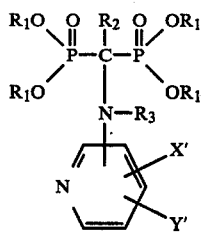

(I)

wherein each of $R_1$, $R_2$ and $R_3$ is independently hydrogen or lower alkyl; and each of X' and Y' is independently hydrogen, halogen, nitro, acetamino, carboxyl, lower alkyl, methoxycarbonyl, hydroxyl or methoxy, provided that, when one valency from the nitrogen atom attached to the carbon atom adjacent to the both phosphorus atoms is on the para-position to the heterocyclic nitrogen atom, one of X' and Y' is independently halogen, nitro, acetamino, carboxyl, lower alkyl, methoxycarbony, hydroxyl or methoxy,
and salts thereof.

Another aspect of the present invention provides a limited class of the compounds of the formula (I), which are represented by the formula:

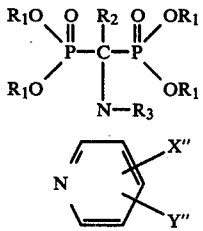

(II)

wherein each of X" and Y" is independently hydrogen, nitro, halogen or lower alkyl; the dotted line is a single bond to be bonded to either of the ortho- or meta-position to the heterocyclic nitrogen atom; and $R_1$, $R_2$, and $R_3$ have each the same meaning as above,
and salts thereof.

A further aspect of the present invention provides a method of use as a herbicide of a compound of the formula:

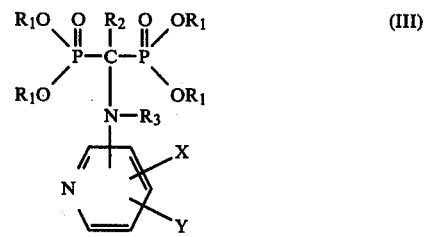

(III)

wherein each of X and Y is independently hydrogen, halogen, nitro, acetamino, carboxyl, lower alkyl, methoxycarbonyl, hydroxyl or methoxy; and $R_1$, $R_2$, and $R_3$ have the same meaning as above,
and salts thereof.

A still further aspect of the present invention provides herbicidal compositions containing as an active ingredient a herbicidally effective amount of the compound of the formula (I), (II) or (III) and an inert carrier therefor and an adjuvant to facilitate the application to plants.

Another still further aspect of the present invention provides a process for producing the compound (III).

The compounds (III) are effective herbicides. Although one of the compounds (III) is known, in which the compound (III) is wherein $R_1$, $R_2$, $R_3$, X, and Y are each hydrogen and one of the bonds from the nitrogen atom attached to the methylenic carbon atom is attached to the para-position to the heterocyclic nitrogen atom, there is no suggestion of any utility in Ploger et al., Zeit. Anog. Anorgan. und Allgem. Chemie, 389, 119 (1972).

In the formulae mentioned hereinabove, the term "lower alkyl" is meant to include an unsaturated, straight or branched chain, aliphatic hydrocarbon residue having a carbon atom range from 1 to 6, preferably 1 to 3. The lower alkyl group may include methyl, ethyl, propyl or isopropyl. The term "halogen" is meant to include chlorine, bromine, fluorine or the like. The single bond from the nitrogen atom attached to the methylenic carbon atom may preferably be bonded to the ortho- or meta-position to the heterocyclic nitrogen atom. The substituent on the pyridine ring may be one or more and preferably include hydrogen, halogen, nitro or lower alkyl and, more preferably, hydrogen, fluorine, nitro, methyl or ethyl. The most preferred substituent on the pyridine ring is methyl and in the ortho-position to the nitrogen atom of the pyridine moiety. The salts of the compounds (III) may include, for example, alkali metal salts, alkali earth metal salts, ammonium salts and organic amine salts.

The compounds (III) may be prepared by the following reaction scheme:

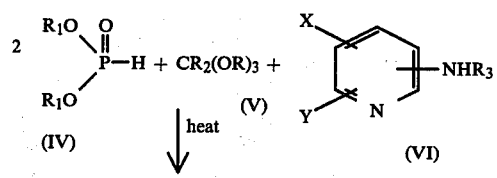

-continued

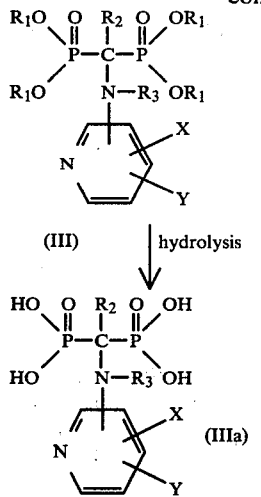

(III)

↓ hydrolysis (IIIa)

wherein $R_1$, $R_2$, $R_3$, X and Y have the same meaning given above and R represents a lower alkyl.

The N-(unsubstituted or substituted pyridyl)-aminomethylenediphosphonic acid esters (III) may be produced, for example, by mixing a dialkyl phosphite (IV), an alkyl ortho-carboxylate (V) and an (unsubstituted or substituted)aminopyridine compound (VI) and heating the mixture, preferably while distilling off the formed alcohol. The esters (III) may be hydrolyzed to provide the corresponding N-(unsubstituted or substituted pyridyl)aminomethylenediphosphonic acids (IIIa).

The dialkyl phosphites (IV) may be di-lower alkyl phosphites in which each of the lower alkyl groups is a straight or branched chain aliphatic hydrocarbon residue having from one to six carbon atoms and may include dimethyl phosphite, diethyl phosphite or dipropyl phosphite. The dialkyl ortho-carboxylates (V) may be lower alkyl ortho-carboxylates in which the lower alkyl group may be a straight or branched chain aliphatic hydrocarbon residue having from one to four carbon atoms and may include methyl ortho-formate, ethyl ortho-formate or propyl ortho-carboxylate; ethyl ortho-carboxylate being preferred. It is preferred from an economical point of view to use 0.5–2.0 moles, preferably 1.0–1.5 moles of the alkyl ortho-carboxylate (V) and 1.5–3.0 moles, preferably 2.0–2.5 moles of the dialkyl phosphite (IV) per mole of the (unsubstituted or substituted)-aminopyridine compound (VI).

The mixture of the compounds (IV), (V) and (VI) may be heated at a temperature of 60° to 190° C., preferably 80° to 150° C. to form the N-(unsubstituted or substituted pyridyl)aminomethylene-diphosphonic acid esters (III).

The hydrolysis of the esters (III) may be carried out in conventional manner. The esters (III) may be subjected to hydrolysis with and without isolation from the reaction mixture. The hydrolysis may be effected by addition of water or a dilute acid such as hydrochloric acid. When the 2-aminopyridine derivatives are used, hydrolysis is particularly easy to be effected by simply boiling in water, whereby the resulting product can be produced in the form of crystals in a high purity.

A temperature range between the boiling point of the lower alcohol of the formula R—OH (in which R has the same meaning given above) and the boiling point of alkyl ortho-formate is preferable as the reaction temperature. In the actual reaction in which, for instance, an oil bath is used, the temperature of the oil bath is maintained around the boiling point of alkyl ortho-formate, whereby the reaction temperature gradually rises starting from the boiling point of the lower alcohol (ROH) while said lower alcohol is distilled out.

The end point of reaction can be seen by the amount of distilled alcohol which has been formed during the reaction.

It is also effective to add a Lewis acid catalyst, such as hydrogen chloride or boron trifluoride, if the progress of the reaction is slow.

The compounds (III), particularly (II), and, more particularly (I), are effective foliar herbicides which can be applied in relatively low concentrations per unit area. Application may be made preferably in the form of liquid or solid compositions to the parts of plants above the soil.

The rates of application depend substantially on the end-use application and on the nature of the application to parts of plant. The conventional rates of application may be between 30 and 1,000 grams of active substance per 10 areas of plant crop.

The herbicidal compounds or substances according to the present invention may be used together with suitable carriers and/or other adjuvants to form solutions, dusts, flowables, wettable powders and aqueous dispersions or emulsions. They may thus be used with a carrier or diluent, e.g. a finely divided solid, an aqueous solution of materials of organic origin, a wetting agent, a dispersing agent, an emulsifying agent or suspension agent, an aqueous emulsion or any desired combination of all these agents.

Aqueous solutions of alkali metal salts, alkali earth metal salts, ammonium salts and organic amine salts, or water-soluble solids may be used. Liquid carriers such as water, alcohols, acetone and dimethyl formamide are also used. The wetting agents, dispersing agents, emulsifying and suspension agents and penetrants are usually known by the collective term "surfactants". Such surfactants may be anionic, cationic or non-ionogenic substances which are known in many varieties. In the manufacture of the compositions according to the present invention the surfactants are usually employed in a concentration of between 1 and 10% by weight.

Dusts and other solid compositions such as granules may be prepared by intimately mixing and/or grinding the active substances with inert solid carriers, e.g. talc, diatomaceous earth, china clay, bentonite, calcium carbonate, limestone, boric acid, dolomite, precipitated silicic acid, alkaline earth metal silicates, mica, tricalcium phosphate and sawdust, powdered cork, clay, bark meal, cellulose powder, charcoal and other materials of vegetable origin. These carriers may be used singly or in admixture with each other. The particle size of the carriers for dusts is advantageously up to about 0.1 mm, for tracking agents between 0.075 to 0.2 mm and for granules from 0.2 mm to 1 mm or more. The carriers also may, however, be impregnated with the active substances by means of a volatile solvent. Dusts and pastes can be suspended in water by adding wetting agents and protective colloids and so used as sprays.

Liquid concentrates for aqueous emulsions and wettable powders for aqueous suspensions may also be prepared from liquid and from solid active substances. Liquid or solid active substances, however, are suitable for manufacturing liquid concentrates or wettable powders of higher concentrations. The various application forms may be adapted to the intended purpose in the conventional manner by adding substances which improve the distribution, the adhesion properties, the resistance to rain and possibly also the absorption. Such substances are in particular the surfactants cited hereinbefore. Likewise it is possible to increase and broaden the biological action by adding substances having bactericidal or fungicidal properties or of other active substances which influence the plant growth, as well as by adding fertilizers.

The herbicidal compositions can be applied to the locus or to the area which is to be protected from weeds in the form of a spray, a powder or dust. The composition may be directly to the locus or to the area which is already infested with weeds. The compositions may thus be applied to the leaves in the form of a spray. On the other hand, the dry compositions in powder form may be scattered directly on to the plants.

The compounds (III) possess a strong herbicidal effect for post-emergence treatment of plants (foliar treatment) and show no herbicidal effect at pre-emergence treatment (soil treatment). The compounds (III) can be used to widely control perennial weeds such as *Imperata cylindrica* Beauv, Johnson grass (*Sorghum halepense*), *Paspalum distichum* L., *Artemisia indica*, *Cyperus rotundus* L. and *Rumex japonicus* Houttuyn which have so far been difficult to weed out. On the other hand, the compounds (III) are scarcely herbicidally active during foliar treatment of cotton. This is an important characteristic feature of the compounds, they are hardly phytotoxic to cotton.

The following examples illustrate the present invention.

EXAMPLE 1

Synthesis of N-[2-(3-methylpyridyl)]aminomethylene-diphosphonic acid

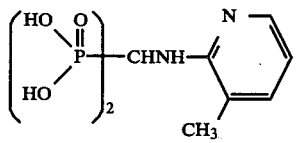
(Compound No. 4)

54.0 g (0.5 mol) of 2-amino-3-methyl-pyridine was mixed with 85.1 g (0.575 mol) of ethyl ortho-formate and 144.9 g (1.05 mol) of diethyl phosphite, and the mixture was heated up to an oil bath temperature of 150° C. in the course of 2 hours, while distilling off the ethanol formed. During this procedure, the temperature gradually rose, starting from around 80° C. at which ethanol began distilling out and approaching the oil bath temperature. The reaction was terminated at the moment when practically no alcohol distillate came out. After the reaction finished, the reaction product was distilled under reduced pressure (130° C./20 mmHg), it produced 199.5 g of tetraethyl N-[2-(3-methylpyridyl)-]aminomethylene-diphosphonate. A part of this product was taken out and purified by thin layer chromatography (carrier:silica gel; solvent:hexane:acetone (1:1)), whereby a pure product melting at 43° C. was obtained.

Next, 60 ml of water was added to the product obtained above and the mixture was heated under reflux for 2 hrs., during which the reaction product turned into a slurry. It was cooled, and then filtered. The solid material was washed with water and then with a small amount of ethanol and dried, whereby 131.2 g (93.0% yield) of crystals of the product compound was obtained. These crystals were almost pure. If recrystallization is necessary, the product is dissolved in concentrated hydrochloric acid which is then distilled off, to form a pure product melting at 297°-298° C.

Elementary analysis of this product gave the following result:

|  | C | H | N |
|---|---|---|---|
| Found | 26.66% | 3.53% | 10.34% |
| Calculated for $C_7H_{12}N_2O_6P_2$ | 26.86% | 3.73% | 10.44% |

EXAMPLE 2

Synthesis of N-[2-(5-chloropyridyl)]aminomethylene-diphosphonic acid

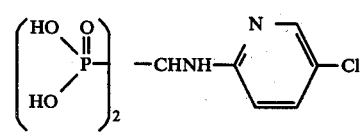
(Compound No. 10)

A mixture of 5.14 g (0.04 mol) of 2-amino-5-chloropyridine, 7.4 g (0.05 mol) of ethyl ortho-formate and 11 g (0.08 mol) diethyl phosphite was heated at 150° C. for 3 hrs, as in Example 1, and the reaction mixture was allowed to stand at room temperature, whereby 11.3 g (68% yield) of tetraethyl N-[2-(5-chloropyridyl)-]aminomethylene-diphosphonate crystals were precipitated from the reaction product. After recrystallization from ether, the melting point of the crystal was 103°-104° C.

5 g of this ester was heated under reflux with 3 ml of concentrated hydrochloric acid on a water bath. The ester, which was dissolved, precipitated as white crystals. After the slurry had been cooled, it was filtered and the crystals were washed with water.

The amount of product obtained was 3.3 g (92% yield).

EXAMPLE 3

Synthesis of N-[2-(6-hydroxycarbonyl)pyridyl-]aminomethylene-diphosphonic acid

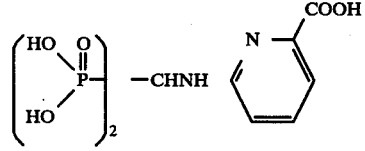
(Compound No. 20)

A mixture of 6.1 g (0.04 mol) of 2-amino-6-methoxycarbonyl-pyridine 7.4 g (0.05 mol) of ethyl ortho-formate and 11 g (0.08 mol) of diethyl phosphite was heated and treated in the same manner as in Example 1 to obtain 11.5 g (66% yield) of crystals of tetraethyl N-[2-(6-methoxycarbonyl)-pyridyl]aminomethylene-diphosphonate. M.P. 104°-106° C.

When 3 g of this ester was heated under reflux on a steam bath, the phosphoric ester moiety and the carboxylic acid ester moiety were simultaneously hydrolyzed, whereby 1.6 g (70% yield) of the captioned object compound precipitated in white crystals. Decomposition at 287°-289° C.

EXAMPLE 4

Synthesis of N-[2-(3-ethoxycarbonyl)pyridyl]aminomethylene-diphosphonic acid

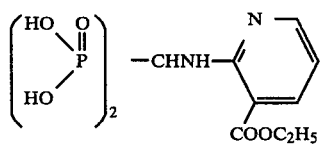

1.66 g (0.01 mol) of 2-amino-3-ethoxycarbonyl-pyridine was mixed with 1.8 g (0.012 mol) of ethyl orthoformate and 2.8 g (0.02 mol) of diethyl phosphite, and the mixture was brought into reaction at 150° C. and heated further to 190° C.

After the reaction had been completed, the reaction product was dissolved in chloroform. The chloroform solution was then washed with water and a brown oily matter was obtained after concentration. This oily matter was hydrolyzed with concentrated hydrochloric acid to give 1.2 g (35% yield) of the product compound. Decomposition at 235°–240° C.

EXAMPLE 5

Synthesis of N-[2-(5-nitropyridyl)]aminomethylene-diphosphonic acid (Compound No. 17)

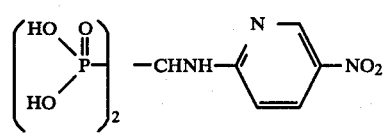

A mixture of 6.95 (0.05 mol) of 2-amino-5-nitropyridine, 9 g (0.06 mol) of ethyl ortho-formate and 13.8 g (0.1 mol) of diethyl phosphite was heated and treated in the same manner as in Example 1 to product 12 g (56% yield) of crystals of tetraethyl N-[2-(5-nitropyridyl)]-aminomethylene-diphosphonate. Melting point 144°–145° C. 5 g of this crystalline product was hydrolyzed with 3 ml of concentrated hydrochloric acid by heating it on a steam bath, whereby 3 g (81% yield) of the captioned product was obtained. Decomposition at 265°–269° C.

EXAMPLE 6

Synthesis of N-[3-(5-methylpyridyl)]aminomethylene-diphosphonic acid (Compound No. 26)

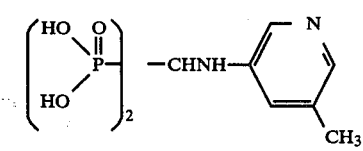

A mixture of 2.2 g (0.2 mol) of 3-amino-5-methyl-pyridine, 3.4 g (0.023 mol) of ethyl ortho-formate and 5.5 g (0.04 mol) of diethyl phosphite was heated and treated in the same manner as in Example 1. The reaction mixture was then allowed to stand at room temperature to precipitate 5.3 g (67% yield) of crystals of tetraethyl N-[3-(5-methyl)-pyridyl]aminomethylene-diphosphonate. M.P. 215°–218° C.

3.0 g of this crystalline product was heated under reflux together with 3 ml of concentrated hydrochloric acid on a steam bath for 8 hrs. After evaporating hydrochloric acid, a small amount of water was added to the residue and the mixture was allowed to stand at room temperature, to form 1.7 g (79% yield) of the product compound in white crystals. Decomposition at 278°–282° C.

EXAMPLE 7

Synthesis of N-(4-pyridyl)aminomethylene-diphosphonic acid (Compound No. 16)

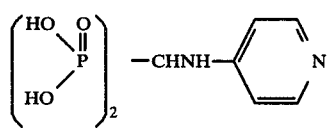

A catalytic amount of trifluoroboron etherate was added to a mixture of 4.7 g (0.05 mol) of 4-aminopyridine and 29.6 g (0.2 mol) of ethyl ortho-formate. The mixture was heated at 130°–140° C. for 4 hrs., while distilling off about 4 g of ethanol formed. After low-boiling matters such as ethanol and the excess amount of ethyl ortho-formate had been removed, 13.8 g (0.1 mol) of diethyl phosphite was added. The mixture was heated at 150° C. for 30 min., while distilling off ethanol formed.

The reaction product was diluted with water and washed with chloroform and the water was removed under reduced pressure. 15 ml of concentrated hydrochloric acid was added into the residue, and the mixture was heated under reflux for 10 hrs. for hydrolysis, whereby 6.1 g (45.4% yield) of the product compound was obtained. Decomposition at 256°–258° C.

In the following Table 1, there are provided a number of compounds obtainable by following one of the above examples.

TABLE 1

| Compound No. | Structural formula | Physical properties |
|---|---|---|
| 1 | $C_2H_5O$–P(=O)(–OC_2H_5)–CH(–NH–2-pyridyl)–P(=O)(OC_2H_5)(OC_2H_5)$ | $N_D^{20} = 1.5068$ (Refractive index) |
| 2 | $C_2H_5O$–P(=O)(–OC_2H_5)–CH(–NH–(3-methyl-2-pyridyl))–P(=O)(OC_2H_5)(OC_2H_5)$ | M.P. 43° C. |
| 3 | $HO$–P(=O)(–OH)–CH(–NH–2-pyridyl)–P(=O)(OH)(OH)$ | 294–295° C. (Dec.) |

TABLE 1-continued
| Compound No. | Structural formula | Physical properties |
|---|---|---|
| 4 | 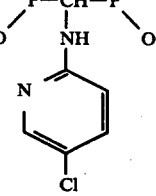 | 297–298° C. (Dec.) |
| 5 | | 268–270° C. (Dec.) |
| 6 | | 274–278° C. (Dec.) |
| 7 | | 293–298° C. (Dec.) |
| 8 | | 278–280° C. (Dec.) |
| 9 | | 255–258° C. (Dec.) |
| 10 | 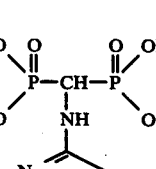 | 285–287° C. (Dec.) |
| 11 | | 279–282° C. (Dec.) |
| 12 | | 295–298° C. (Dec.) |
| 13 | | over 300° C. (Dec.) |
| 14 | | 258–267° C. (Dec.) |
| 15 | | over 300° C. (Dec.) |

TABLE 1-continued

| Compound No. | Structural formula | Physical properties |
|---|---|---|
| 16* | (HO)(HO)P(=O)–CH(NH-3-pyridyl)–P(=O)(OH)(OH) | 256–258° C. (Dec.) |
| 17 | (HO)(HO)P(=O)–CH(NH-(5-nitro-2-pyridyl))–P(=O)(OH)(OH) | 265–269° C. (Dec.) |
| 18 | (C₂H₅O)(C₂H₅O)P(=O)–CH(NH-(5-nitro-2-pyridyl))–P(=O)(OC₂H₅)(OC₂H₅) | M.P. 144–145° C. |
| 19 | (HO)(HO)P(=O)–CH(NH-(4,6-dimethyl-2-pyridyl))–P(=O)(OH)(OH) | 309–313° C. (Dec.) |
| 20 | (HO)(HO)P(=O)–CH(NH-(6-carboxy-2-pyridyl))–P(=O)(OH)(OH) | 287–289° C. (Dec.) |
| 21 | (C₂H₅O)(C₂H₅O)P(=O)–CH(NH-(6-methoxycarbonyl-2-pyridyl))–P(=O)(OC₂H₅)(OC₂H₅) | M.P. 104–106° C. |
| 22 | (C₂H₅O)(C₂H₅O)P(=O)–CH(NH-(6-acetamido-2-pyridyl))–P(=O)(OC₂H₅)(OC₂H₅) | M.P. 180–190° C. |
| 23 | (HO)(HO)P(=O)–CH(NH-(6-hydroxy-3-pyridyl))–P(=O)(OH)(OH) | 284–287° C. (Dec.) |
| 24 | (HO)(HO)P(=O)–CH(NH-(6-methoxy-3-pyridyl))–P(=O)(OH)(OH) | 258–261° C. (Dec.) |
| 25 | (HO)(HO)P(=O)–CH(NH-(3,4-dimethyl-2-pyridyl))–P(=O)(OH)(OH) | 268–272° C. (Dec.) |
| 26 | (HO)(HO)P(=O)–CH(NH-(5-methyl-3-pyridyl))–P(=O)(OH)(OH) | 278–282° C. (Dec.) |
| 27 | (HO)(HO)P(=O)–CH(NH-(2-methyl-4-pyridyl))–P(=O)(OH)(OH) | over 300° C. (Dec.) |

TABLE 1-continued

| Compound No. | Structural formula | Physical properties |
|---|---|---|
| 28 | [aminomethylene bisphosphonic acid with 3-methoxypyridin-2-yl NH substituent] | 267–270° C. (Dec.) |
| 29 | [aminomethylene bisphosphonic acid with 6-chloropyridin-4-yl NH substituent] | 293–294° C. (Dec.) |
| 30 | [aminomethylene bisphosphonic acid with 3-fluoropyridin-4-yl NH substituent] | 243–248° C. (Dec.) |
| 31 | [aminomethylene bisphosphonic acid with 4-nitropyridin-2-yl NH substituent] | 248–250° C. (Dec.) |
| 32 | [aminomethylene bisphosphonic acid with 3-methyl-5-bromopyridin-2-yl NH substituent] | 293–294° C. (Dec.) |
| 33 | [aminomethylene bisphosphonic acid with 3-methyl-5-nitropyridin-2-yl NH substituent] | 250–260° C. (Dec.) |
| 34 | [aminomethylene bisphosphonic acid with 3-fluoropyridin-2-yl NH substituent] | 277–280° C. (Dec.) |
| 35 | [aminomethylene bisphosphonic acid with 3-chloropyridin-2-yl NH substituent] | 294–296° C. (Dec.) |
| 36 | [aminomethylene bisphosphonic acid with 5-fluoropyridin-2-yl NH substituent] | 270–280° C. (Dec.) |
| 37 | [aminomethylene bisphosphonic acid with 3-methyl-5-fluoropyridin-2-yl NH substituent] | 286–288° C. (Dec.) |
| 38 | [aminomethylene bisphosphonic acid with 3-chloropyridin-4-yl NH substituent] | 270–275° C. (Dec.) |
| 39 | [tetramethyl ester of aminomethylene bisphosphonate with 3-methylpyridin-2-yl NH substituent] | M.P. 90–93° C. |
| known compound ** | $CH_3-{}^+N$―[bipyridyl]―$N^+{=}CH_3$  $Cl^-$  $Cl^-$  (generic name: Paraquat) | over 300° C. (Dec.) |

*The compound No. 16 is described in Zeitschrift fur Anorganische und Allgemeine Chemie, Vol. 389, p. 119 (1972).
**The known compound with the generic name Paraquat was used as a control in the following Text Example 6.

In the following example, formulation of herbicides that contain the Invention Compounds as active ingredients will be illustrated in detail. However, the present invention is not limited to the formulation examples. The term "parts" means parts by weight.

EXAMPLE 8

| Wettable powder | |
|---|---|
| Compound No. 3 | 25 parts |
| Zieclite A (Commercial name) | 69 parts |
| Sorpol 5039 (a product of Toho Chem. Co.) | 3 parts |
| Carplex | 3 parts |
| (Congelation inhibitor of Shionogi Pharmaceutical Co.) | |

The above components were homogeneously blended and crushed to prepare a wettable powder. Upon application, the above wettable powder is diluted 50–1,000 times with water and scattered in such an active ingredient amount as 30–1,000 g per 10 ares.

EXAMPLE 9

| Aqueous solution | |
|---|---|
| Compound No. 4 | 30 parts |
| Diethanolamine | 11.7 parts |
| Water | 58.3 parts |

The above components were completely blended and dissolved to prepare an aqueous solution. Upon application, the above aqueous solution was diluted 50–1,000 times with water and scattered in such an active ingredient amount as 30–1,000 g per 10 ares.

TEST EXAMPLE 1

An aqueous solution prepared in the same manner as in Example 9, which contain Compound No. 4, prior art Compound No. 16, prior art Compound No. 2f (=N-phenylmethyl-aminomethylene diphosphonic acid) and prior art Compound No. 2h(=N-(2,4,6-trimethylphenyl)aminomethylene diphosphonic acid, respectively, was used to evaluate their respective herbicidal effects. The aqueous solution was diluted to contain an amount of active substance as shown in the following Table 1 and scattered onto leaves and stalks. The test results were observed 14 days after application. The results are shown in Table 2, in which the ratings are the same as described at page 36 of this specification.

Hiern, and Cucumber plants, when applied in the amounts of 25 and 12.5 grams per acre, respectively, were lowered from ratings 5 to 4, i.e. down to until 70 percent.

The test Compound No. 16 generally showed excellent effects when applied in the amounts of 100 grams per acre; however, the herbicidal activities were decreased rapidly and in significant manner, in some cases even to null when applied in the amount of 25 grams per acre, whereas the Compound No. 4 when applied in the same amount as above indicated still excellent herbicidal activities.

The herbicidal activity of the Compound No. 16 against rice plants was lowered to rating 2 even when applied in the amount of 50 grams per acre, whereas the rating of the Compound No. 4 was still 5. Its activity became null in the amounts of 25 and 12.5 grams per acre, respectively. In these amounts, the Compound No. 4 possessed rating 4 activities.

The herbicidal activities of the Compound No. 16 against *Chenopodium ficifolium* Smith, *Portulaca oleracea* L., and *Galinsoga parviflora* Cav. were down to rating 4 in the amounts of 50 grams per acre, to rating 3 in the amounts of 25 grams per acre, and to rating 2 in the amounts of 12.5 grams per acre; whereas the Compound No. 4 maintained its herbicidal activities to the highest level in the same amounts.

The herbicidal activities of the Compound No. 16 against *Cyperus microiria* Steud and *Rorippa indica* Hiern were lowered from rating 5 to rating 3 in the amounts of 50 grams per acre, to rating 2 in the amount of 25 grams per acre, and to rating 0 in the amounts of 12.5 grams per acre. However, the activities of the Compound No. 4 were between the ratings 5 and 4 in the same amounts.

The Compound No. 16 lowered its herbicidal effects on *Digitaria adscendens* Henr., tomato and cucumber plants to ratings 3 or 2 when applied in the amounts of 25 grams per acre and to ratings 3 or 1 in the amounts of 12.5 grams per acre. The Compound No. 4 still had the excellent good herbicidal activities against them.

The test Compounds No. 2f and 2h showed no or little herbicidal activities against the test plants even in

TABLE 2

| | Amounts of Application (grams/acre) | | | | | | | | | |
|---|---|---|---|---|---|---|---|---|---|---|
| | Compound No. 4 | | | | Compound No. 16 | | | | Compound No. 2f | Compound No. 2h |
| Test Plants | 100 | 50 | 25 | 12.5 | 100 | 50 | 25 | 12.5 | 100 | 100 |
| Rice plant | 5 | 5 | 4 | 4 | 5 | 2 | 0 | 0 | 0 | 0 |
| *Digitaria adscendens* Henr. | 5 | 5 | 5 | 5 | 5 | 5 | 2 | 1 | 2 | 2 |
| *Cyperus microiria* Steud | 5 | 5 | 5 | 5 | 5 | 3 | 2 | 0 | 1 | 1 |
| *Chenopodium ficifolium* Smith | 5 | 5 | 5 | 5 | 5 | 4 | 3 | 2 | 2 | 2 |
| *Portulaca oleracea* L. | 5 | 5 | 5 | 5 | 5 | 4 | 3 | 2 | 0 | 0 |
| *Rorippa indica* Hiern | 5 | 5 | 4 | 4 | 5 | 3 | 2 | 0 | 2 | 0 |
| *Galinsoga parviflora* Cav. | 5 | 5 | 5 | 5 | 5 | 4 | 3 | 2 | 0 | 0 |
| Tomato plant | 5 | 5 | 5 | 5 | 5 | 5 | 3 | 3 | 0 | 0 |
| Cucumber plant | 5 | 5 | 4 | 4 | 5 | 5 | 3 | 3 | 0 | 1 |

Note:
Ratings for the test results are determined in the same manner as disclosed on page 36 of the specification of the present invention.

The tests demonstrate that Compound No. 4 of the present invention had excellent herbicidal effects on most of the plants tested when applied in the amounts of 100, 50, 25 and 12.5 grams per acre; the activities of the Compound No. 4 against rice plants, *Rorippa indica* the amount of 100 grams per acre.

TEST EXAMPLE 2

The following compounds were tested in substantially the same manner as in Test Example 1, when used in low concentrations. The results are shown in Table 3.

tion Compound was applied to stalks and leaves at a rate of 100 g/a.

TABLE 3

| Compound Nos. | Amount of Active Substance (g/a) | Rice Plant | Weeds (a) | (b) | (c) | (d) | (e) | (f) | Tomato | Cucumber |
| --- | --- | --- | --- | --- | --- | --- | --- | --- | --- | --- |
| 3. | 50 | 5 | 5 | 5 | 5 | 5 | 5 | 5 | 5 | 5 |
|  | 25 | 4 | 5 | 5 | 5 | 5 | 5 | 5 | 5 | 5 |
|  | 12.5 | 4 | 5 | 5 | 5 | 5 | 5 | 5 | 5 | 4 |
|  | 6.25 | 3 | 5 | 4 | 5 | 5 | 4 | 4 | 5 | 4 |
| 4. | 50 | 5 | 5 | 5 | 5 | 5 | 5 | 5 | 5 | 5 |
|  | 25 | 5 | 5 | 5 | 5 | 5 | 5 | 5 | 5 | 5 |
|  | 12.5 | 5 | 5 | 5 | 5 | 5 | 5 | 5 | 5 | 5 |
|  | 6.25 | 3 | 5 | 5 | 5 | 5 | 5 | 5 | 5 | 4 |
| 5. | 50 | 3 | 5 | 5 | 5 | 5 | 5 | 5 | 5 | 5 |
|  | 25 | 2 | 5 | 5 | 5 | 5 | 4 | 5 | 5 | 4 |
|  | 12.5 | 2 | 4 | 5 | 5 | 5 | 3 | 5 | 5 | 4 |
|  | 6.25 | 1 | 3 | 3 | 3 | 5 | 2 | 4 | 2 | 2 |
| 6. | 50 | 4 | 5 | 5 | 5 | 5 | 5 | 5 | 5 | 5 |
|  | 25 | 3 | 5 | 5 | 5 | 5 | 4 | 5 | 5 | 5 |
|  | 12.5 | 2 | 5 | 5 | 5 | 5 | 2 | 5 | 5 | 4 |
|  | 6.25 | 1 | 4 | 4 | 5 | 5 | 2 | 4 | 4 | 4 |
| 8. | 50 | 5 | 5 | 5 | 5 | 5 | 5 | 5 | 5 | 5 |
|  | 25 | 5 | 5 | 5 | 5 | 5 | 5 | 5 | 5 | 5 |
|  | 12.5 | 5 | 5 | 5 | 5 | 5 | 5 | 5 | 5 | 5 |
|  | 6.25 | 4 | 5 | 5 | 5 | 4 | 5 | 5 | 5 | 4 |
| 9. | 50 | 3 | 5 | 5 | 5 | 4 | 4 | 4 | 4 | 5 |
|  | 25 | 2 | 4 | 5 | 4 | 3 | 4 | 3 | 4 | 4 |
|  | 12.5 | 1 | 4 | 5 | 3 | 2 | 4 | 3 | 3 | 3 |
|  | 6.25 | 1 | 3 | 4 | 3 | 2 | 3 | 3 | 3 | 3 |
| 13. | 50 | 5 | 5 | 5 | 5 | 5 | 5 | 5 | 5 | 4 |
|  | 25 | 4 | 5 | 4 | 5 | 3 | 3 | 5 | 5 | 4 |
|  | 12.5 | 4 | 5 | 4 | 5 | 2 | 2 | 5 | 5 | 3 |
|  | 6.25 | 3 | 4 | 3 | 4 | 2 | 2 | 4 | 4 | 3 |
| 15. | 50 | 3 | 5 | 4 | 5 | 5 | 4 | 5 | 5 | 3 |
|  | 25 | 2 | 5 | 2 | 5 | 5 | 3 | 4 | 5 | 2 |
|  | 12.5 | 2 | 4 | 1 | 4 | 2 | 2 | 4 | 4 | 2 |
|  | 6.25 | 1 | 4 | 1 | 4 | 2 | 1 | 3 | 4 | 2 |
| 25. | 50 | 4 | 5 | 5 | 5 | 5 | 5 | 5 | 5 | 5 |
|  | 25 | 4 | 5 | 5 | 5 | 4 | 5 | 5 | 5 | 5 |
|  | 12.5 | 3 | 4 | 4 | 5 | 2 | 5 | 4 | 5 | 4 |
|  | 6.25 | 3 | 4 | 4 | 4 | 2 | 4 | 4 | 4 | 4 |
| 26. | 50 | 2 | 5 | 5 | 5 | 5 | 5 | 5 | 5 | 5 |
|  | 25 | 2 | 5 | 5 | 5 | 4 | 5 | 5 | 5 | 5 |
|  | 12.5 | 1 | 3 | 5 | 4 | 3 | 4 | 3 | 4 | 4 |
|  | 6.25 | 1 | 3 | 4 | 4 | 3 | 4 | 3 | 4 | 4 |
| 31. | 50 | 5 | 5 | 5 | 5 | 5 | 5 | 5 | 5 | 5 |
|  | 25 | 4 | 5 | 5 | 5 | 4 | 5 | 3 | 5 | 4 |
|  | 12.5 | 4 | 5 | 5 | 4 | 4 | 4 | 2 | 4 | 3 |
|  | 6.25 | 3 | 4 | 4 | 4 | 3 | 4 | 2 | 4 | 3 |
| 34. | 50 | 5 | 5 | 5 | 5 | 5 | 5 | 5 | 5 | 5 |
|  | 25 | 4 | 5 | 5 | 5 | 5 | 5 | 5 | 5 | 5 |
|  | 12.5 | 4 | 5 | 5 | 5 | 5 | 5 | 5 | 5 | 5 |
|  | 6.25 | 4 | 5 | 5 | 4 | 5 | 5 | 3 | 5 | 4 |
| 16. | 50 | 3 | 5 | 4 | 5 | 5 | 5 | 5 | 5 | 5 |
|  | 25 | 2 | 4 | 3 | 4 | 3 | 4 | 3 | 4 | 4 |
|  | 12.5 | 1 | 3 | 2 | 3 | 3 | 3 | 3 | 3 | 4 |
|  | 6.25 | 0 | 2 | 2 | 3 | 2 | 1 | 2 | 3 | 2 |

Notes:
(a) = *Digitaria adscendens* Hener.
(b) = *Cyperus microiria* Steud
(c) = *Chenopodium ficifolium* Smith
(d) = *Portulaca oleracea* L.
(e) = *Rorippa indica* Hiern
(f) = *Galinsoga parviflora* Cav.

TEST EXAMPLE 3

Test on herbicidal effect by foliar treatment

Diluvial soil was placed in a plastic box 15 cm long, 22 cm broad and 6 cm deep. Seeds of rice, Digitaria adscendens Henr., Cyperus microiria Steud, Chenopodium ficifolium Smith, Portulaca oleracea L., Rorippa indica Hiern, Galinsoga parviflora Cav, Tomato, and cucumber were sowed spot-wise and covered with soil about 1.5 cm thick. When rice, tomato, cucumber and the various weeds had reached 3-leaf stage, the Invention Compound was applied to stalks and leaves at a rate of 100 g/a.

The wettable powder of the aforementioned Formulation Example 8 was diluted with water and was scattered by a small spray all over the surface of stalks and leaves of rice, cucumber, tomato and the various weeds.

Two weeks after application of the herbicide, its herbicidal efficacy against rice, tomato, cucumber and the various weeds was evaluated based on the following standard. The results are summarized in Table 4. Evaluation ratings are as follows:

5 ... herbicidal rate above 90%
4 ... herbicidal rate 70-90%
3 ... herbicidal rate 40-70%

2 ... herbicidal rate 20-40%
1 ... herbicidal rate 5-20%
0 ... herbicidal rate below 5% (practically no efficacy)

The above herbicidal rate was calculated by the following equation based on the weight measured of the live plants above soil in the herbicide-treated and the untreated plot:

Herbicidal rate (%) =

$$\left(1 - \frac{\text{weight of live plant above soil in herbicide - treated plot}}{\text{weight of live plant above soil in herbicide - untreated plot}}\right) \times 100$$

TEST EXAMPLE 4

Test on herbicidal effect at foliar treatment

The aqueous solution of the aforementioned Formulation Example 9 was diluted and scattered on leaves and stalks in such a way that the application amount of the Invention Compound was 25 g/a, 12.5 g/a and 6.3 g/a. The test was carried out in the same manner as in Test Example 3. In the present test, also cotton seed was included.

The herbicidal effect was examined in accordance with the evaluation standard mentioned in Test Example 3. The results are summarized in Table 5.

TABLE 4

| Compound No. | Application amount of active ingredient (g/a) | Rice | Digitaria adscendens Henr. | Cyperus microiria Steud | Chenopodium ficifolium Smith | Portulaca oleracea L. | Rorippa indica Hiern | Galinsoga parviflora Cav. | Tomato | Cucumber |
|---|---|---|---|---|---|---|---|---|---|---|
| 1 | 100 | 0 | 4 | 2 | 2 | 4 | 3 | 3 | 1 | 2 |
| 2 | " | 3 | 5 | 4 | 4 | 5 | 2 | 2 | 2 | 2 |
| 3 | " | 3 | 5 | 5 | 5 | 5 | 5 | 5 | 5 | 5 |
| 4 | " | 4 | 5 | 5 | 5 | 5 | 5 | 5 | 5 | 5 |
| 5 | " | 1 | 5 | 5 | 5 | 5 | 5 | 5 | 5 | 5 |
| 6 | " | 3 | 5 | 5 | 5 | 5 | 5 | 5 | 5 | 5 |
| 7 | " | 0 | 3 | 3 | 3 | 3 | 4 | 2 | 3 | 3 |
| 8 | " | 4 | 4 | 5 | 5 | 5 | 5 | 5 | 5 | 5 |
| 9 | " | 4 | 4 | 5 | 5 | 5 | 5 | 5 | 5 | 5 |
| 10 | " | 2 | 3 | 5 | 5 | 4 | 5 | 5 | 5 | 5 |
| 11 | " | 0 | 3 | 5 | 4 | 4 | 5 | 4 | 5 | 5 |
| 12 | " | 0 | 5 | 5 | 5 | 2 | 5 | 3 | 5 | 4 |
| 13 | " | 5 | 5 | 5 | 5 | 3 | 5 | 5 | 5 | 5 |
| 14 | " | 0 | 1 | 3 | 3 | 5 | 5 | 4 | 5 | 3 |
| 15 | " | 3 | 5 | 5 | 5 | 5 | 4 | 5 | 5 | 4 |
| 16 | " | 5 | 5 | 5 | 5 | 5 | 5 | 5 | 5 | 5 |
| 17 | " | 0 | 1 | 0 | 2 | 0 | 0 | 2 | 3 | 2 |
| 18 | " | 0 | 2 | 0 | 2 | 0 | 0 | 2 | 1 | 3 |
| 19 | " | 0 | 1 | 2 | 1 | 0 | 0 | 2 | 2 | 1 |
| 20 | " | 0 | 1 | 0 | 3 | 0 | 2 | 2 | 0 | 2 |
| 21 | " | 0 | 0 | 0 | 0 | 0 | 0 | 2 | 0 | 0 |
| 22 | " | 0 | 1 | 0 | 0 | 0 | 1 | 2 | 0 | 0 |
| 23 | " | 0 | 0 | 0 | 0 | 0 | 1 | 0 | 0 | 0 |
| 24 | " | 0 | 0 | 0 | 1 | 0 | 1 | 0 | 0 | 0 |
| 25 | " | 5 | 5 | 5 | 5 | 5 | 5 | 5 | 5 | 5 |
| 26 | " | 2 | 5 | 5 | 5 | 5 | 5 | 5 | 5 | 5 |
| 27 | " | 3 | 5 | 5 | 5 | 5 | 5 | 5 | 5 | 5 |
| 28 | " | 2 | 3 | 4 | 5 | 3 | 4 | 3 | 4 | 4 |
| 29 | " | 3 | 4 | 4 | 4 | 3 | 5 | 3 | 4 | 3 |
| 30 | " | 3 | 4 | 5 | 5 | 5 | 5 | 4 | 5 | 5 |
| 31 | " | 4 | 5 | 5 | 5 | 5 | 5 | 5 | 5 | 5 |
| 32 | " | 3 | 5 | 4 | 5 | 3 | 4 | 5 | 5 | 5 |
| 33 | " | 3 | 5 | 3 | 3 | 2 | 2 | 1 | 3 | 3 |
| 34 | " | 5 | 5 | 5 | 5 | 5 | 5 | 5 | 5 | 5 |
| 35 | " | 4 | 5 | 5 | 5 | 5 | 4 | 5 | 5 | 5 |
| 36 | " | 5 | 5 | 5 | 5 | 5 | 5 | 5 | 5 | 5 |
| 37 | " | 4 | 4 | 5 | 5 | 3 | 5 | 4 | 4 | 5 |
| 38 | " | 4 | 5 | 5 | 5 | 4 | 3 | 5 | 5 | 5 |
| 39 | " | 3 | 5 | 4 | 5 | 5 | 5 | 5 | 5 | 4 |

TABLE 5

| Compound No. | Application amount of active ingredient (g/a) | Rice | Digitaria adscendens Henr. | Cyperus microiria Steud | Chenopodium ficifolium Smith | Portulaca oleracea L. | Rorippa indica Hiern | Galinsoga parviflora Cav. | Tomato | Cucumber | Cotton |
|---|---|---|---|---|---|---|---|---|---|---|---|
| 3 | 25 | 3 | 5 | 4 | 5 | 5 | 3 | 5 | 5 | 3 | 0 |
|  | 12.5 | 0 | 4 | 4 | 5 | 5 | 2 | 3 | 4 | 1 | 0 |
|  | 6.3 | 0 | 4 | 3 | 2 | 5 | 1 | 2 | 2 | 1 | 0 |
| 4 | 25 | 3 | 5 | 5 | 5 | 5 | 4 | 5 | 5 | 5 | 0 |
|  | 12.5 | 3 | 5 | 5 | 5 | 5 | 4 | 5 | 5 | 3 | 0 |
|  | 6.3 | 0 | 5 | 4 | 5 | 3 | 4 | 4 | 5 | 2 | 0 |
| 5 | 25 | 1 | 5 | 4 | 5 | 5 | 3 | 4 | 4 | 3 | 0 |
|  | 12.5 | 1 | 3 | 4 | 5 | 5 | 1 | 3 | 4 | 3 | 0 |

TABLE 5-continued

| Compound No. | Application amount of active ingredient (g/a) | Rice | Digitaria adscendens Henr. | Cyperus microiria Steud | Chenopodium ficifolium Smith | Portulaca oleracea L. | Rorippa indica Hiern | Galinsoga parviflora Cav. | Tomato | Cucumber | Cotton |
|---|---|---|---|---|---|---|---|---|---|---|---|
| 6 | 25 | 2 | 5 | 4 | 5 | 5 | 3 | 4 | 5 | 4 | 0 |
|   | 12.5 | 1 | 5 | 4 | 5 | 5 | 0 | 4 | 5 | 3 | 0 |
| 13 | 25 | 3 | 5 | 3 | 5 | 1 | 1 | 5 | 5 | 2 | 0 |
|   | 12.5 | 3 | 4 | 3 | 5 | 0 | 0 | 4 | 5 | 1 | 0 |
| 16 | 25 | 2 | 4 | 3 | 4 | 3 | 4 | 3 | 4 | 4 | 0 |
|   | 12.5 | 1 | 3 | 2 | 3 | 3 | 3 | 3 | 3 | 4 | 0 |

As is seen from Table 4, the Invention Compounds have little herbicidal activity against cotton.

TEST EXAMPLE 5

Test on herbicidal effect as soil treatment

Disinfected diluvial soil was placed in a plastic box 15 cm long, 22 cm broad, and 6 cm deep. Seeds of rice, Panicum Crus-galli L., Digitaria adscendens Henr., Cyperus microiria Steud, Chenopodium ficifolium Smith, Portulaca oleracea L., Rorippa indica Hiern, and Galinsoga parviflora Cav. were sowed mixed and covered with soil about 1.5 cm thick. 100 g/a of the compound of the present invention was applied over the surface of soil. The wettable powder of the aforementioned Formulation Example 8 was diluted with water and the liquid thus prepared was applied by a small spray all over the surface.

Three weeks after application, the herbicidal effect against rice and the various weeds was examined according to the evaluation standard described in Test Example 3. The results are shown in Table 6.

TABLE 6

| Compound No. | Application amount of active ingredient (g/a) | Rice | Digitaria adscendens Henr. | Cyperus microiria Steud | Chenopodium ficifolium Smith | Portulaca oleracea L. | Rorippa indica Hiern | Galinsoga parviflora Cav. |
|---|---|---|---|---|---|---|---|---|
| 1 | 100 | 0 | 1 | 1 | 0 | 0 | 1 | 0 |
| 3 | " | 0 | 0 | 0 | 0 | 0 | 0 | 0 |
| 4 | " | 0 | 0 | 0 | 0 | 0 | 0 | 0 |
| 5 | " | 0 | 0 | 0 | 0 | 0 | 0 | 0 |
| 6 | " | 0 | 0 | 0 | 0 | 0 | 0 | 0 |
| 13 | " | 0 | 0 | 0 | 0 | 0 | 0 | 0 |

TEST EXAMPLE 6

Test on herbicidal effect against perennial weed at foliar treatment

Terrestrial stems and root tubers each of Imperata cylindrica Beauv, Rumex japonicus Houttuyn, Johnson grass, Artemisia vulgaris L. var. indica Maxim, Cyperus rotundus L. and Paspalum distichum L. were gathered out in the fields. Imperata cylindrica Beauv and Rumex japonicus Houttuyn were transplanted each in a Wagner pot of an area of 1/5000 acre, Johnson grass, Artemisia vulgaris L. var. indica Maxim and Cyperus rotundus L. each in a 5-inch flowerpot, and Paspalum distichum L. was transplanted in a plastic box 15 cm long, 22 cm broad and 6 cm deep. These weeds were sufficiently grown in a greenhouse for a period of 45-90 days and the Invention Compound and the control compound were each applied to stems and leaves of the above mentioned perennial weeds to such an extent that their application amount per unit of area reaches a prescribed value.

The water-soluble liquid preparation of the aforementioned Formulation Example 9 was diluted with water and the preparation thus diluted was applied all over the surface of stems and leaves of the weeds by a small spray.

One month after herbicide application, the herbicidal effect against the above mentioned perennial weeds was examined in accordance with the evaluation standard described in Test Example 3. The results are shown in Table 7.

After examination of this herbicidal effect (herbicidal rate), the terrestrial part of each plant was completely cut off and then the recovery rate at one month thereafter of the weeds was examined according to the following evaluation standard: The result is indicated in Table 7. Evaluation ratings are as follows:

5 ... recovery rate below 10%
4 ... recovery rate 10-30%
3 ... recovery rate 30-60%
2 ... recovery rate 60-80%
1 ... recovery rate 80-95%
0 ... recovery rate above 95% (which approximately corresponds to untreated plot)

The recovery rate was calculated by the following equation based on the weight measured of the terrestrial part of the live plants in the herbicide-treated and the untreated plot:

$$\text{Recovery rate} = \left( \frac{\text{weight of terrestrial part of plants in herbicide — treated plot}}{\text{weight of terrestrial part of plants in herbicide — untreated plot}} \right) \times 100$$

TABLE 7

| Compound No. | Application amount of active ingredient (g/a) | | Imperata cylindrica Beauv | Rumex japonicus Houttuyn | Johnson grass | Artemisia indica | Cyperus rotundus | Paspalum distichum L. |
|---|---|---|---|---|---|---|---|---|
| 3 | 30 | Herbicidal rate | 4 | 5 | 5 | 4 | 5 | 4 |
|   |    | Recovery rate  | 3 | 4 | 4 | 2 | 3 | 4 |
| 4 | 30 | Herbicidal rate | 5 | 5 | 5 | 5 | 5 | 5 |
|   |    | Recovery rate  | 5 | 5 | 5 | 3 | 4 | 5 |
| Control Compound* | 7.5 | Herbicidal rate | 5 | 5 | 5 | 5 | 5 | 5 |
|   |    | Recovery rate  | 2 | 0 | 2 | 1 | 3 | 0 |

*Paraquat (generic name) was used as the control compound.

The compounds (III) show a high herbicidal effect against perennial weeds as well as activity against subterranean parts of these plants, thereby very strongly controlling re-emergence of the weeds.

What is claimed is:

1. A compound of the formula

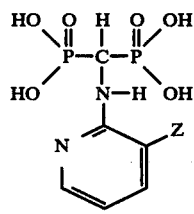

wherein Z denotes hydrogen, an alkyl group having 1-3 carbon atoms or a halogen.

2. The compound of claim 1 wherein Z denotes hydrogen.
3. The compound of claim 1 wherein Z denotes methyl.
4. The compound of claim 1 wherein Z denotes ethyl.
5. The compound of claim 1 wherein Z denotes fluorine.
6. A herbicidal composition comprising a herbicidally effective amount of a compound of the formula

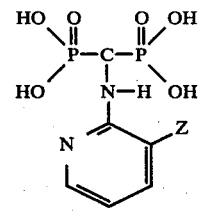

wherein Z denotes hydrogen, an alkyl group having 1-3 carbon atoms or a halogen, or a salt thereof.

7. The composition of claim 6 wherein Z denotes hydrogen.
8. The composition of claim 6 wherein Z denotes methyl.
9. The composition of claim 6 wherein Z denotes ethyl.
10. The composition of claim 6 wherein Z denotes fluorine.
11. A method of controlling weeds comprising: applying to the surfaces of weeds a weed-controlling effective amount of a compound of the formula

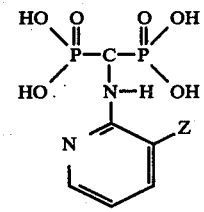

wherein Z denotes hydrogen, an alkyl group having 1-3 carbon atoms or a halogen or a salt thereof.

12. The method of claim 11 wherein Z denotes hydrogen.
13. The method of claim 11 wherein Z denotes methyl.
14. The method of claim 11 wherein Z denotes ethyl.
15. The method of claim 11 wherein Z denotes fluorine.

* * * * *